United States Patent [19]
Lin

[11] Patent Number: 5,659,100
[45] Date of Patent: *Aug. 19, 1997

[54] PRODUCTION OF VINYLIDENE OLEFINS

[75] Inventor: Kaung-Far Lin, Baton Rouge, La.

[73] Assignee: Amoco Corporation, Chicago, Ill.

[*] Notice: The term of this patent shall not extend beyond the expiration date of Pat. No. 5,625,105.

[21] Appl. No.: 596,801

[22] Filed: Feb. 5, 1996

[51] Int. Cl.$^6$ ................................. C10M 143/00
[52] U.S. Cl. ..................... 585/503; 585/511; 585/512
[58] Field of Search ..................... 585/503, 511, 585/512

[56] References Cited

U.S. PATENT DOCUMENTS

| | | | |
|---|---|---|---|
| 4,155,946 | 5/1979 | Sato et al. | 585/513 |
| 4,709,112 | 11/1987 | Sato et al. | 585/513 |
| 4,795,851 | 1/1989 | Frame et al. | 585/512 |
| 4,973,788 | 11/1990 | Lin et al. | 585/511 |
| 5,124,465 | 6/1992 | Allen et al. | 556/190 |
| 5,516,958 | 5/1996 | Schaerfl, Jr. et al. | 585/511 |

OTHER PUBLICATIONS

Ziegler, et al., *Justus Liebigs Ann. Chem.*, vol. 629, pp. 1–74 (Mar. 1960) Translation.
*The Use of Aluminum Alkyls in Organic Synthesis*, Ethyl Corporation, pp. 1–75, (2nd Printing, Mar., 1977).

*Primary Examiner*—Jacqueline V. Howard
*Attorney, Agent, or Firm*—James R. Henes; Stephen L. Hensley

[57] ABSTRACT

Vinylidene olefin can be formed in good yield and high selectivity in much shorter reaction periods than found critical heretofore. The process involves dimerizing vinyl olefin with at least one trialkylaluminum compound as the sole catalyst component charged to the reaction vessel. These materials are charged to the reactor so that it contains in the range of 0.001 to 0.5 mol of trialkylaluminum per mol of the initial vinyl olefin. The reaction is performed at a temperature in the range of 100° to 200° C. for a period of time sufficient to convert 10 to 99% by weight of the initial vinyl olefin to a different product and form a product mixture with at least 80 wt % vinylidene dimer selectivity. In conducting the process the liquid mixture in the reactor is maintained in direct contact with passivated ferrous metal such as low nickel ferrous metal or steel alloy interior surfaces during at least 90 percent of the total period of time during which the reactor contents are at a temperature above about 50° C.

40 Claims, No Drawings

PRODUCTION OF VINYLIDENE OLEFINS

TECHNICAL FIELD

This invention relates to an improved process enabling the production of vinylidene olefins in good yields with high selectivities.

BACKGROUND

Vinylidene olefin, which are branched monoolefins having the structure $(R^1)(R^2)C=CH_2$ where $R^1$ and $R^2$ are the same or, more usually, different alkyl groups, are of commercial importance as raw materials for use in producing-double tailed oxo alcohols and other functionalized derivatives, used in the manufacture of detergents, surfactants, specialty agricultural chemicals, and fuel or lubricant additives. Vinylidene olefins can be produced by dimerizing vinyl olefins.

U.S. Pat. No. 4,155,946 to Sato, Noguchi and Yasui discloses a process for dimerizing lower α-olefins in which the catalyst system is formed from (1) a trialkylaluminum compound, (2) a salt or complex of nickel, (3) a trivalent phosphorus compound selected from specified groups, and (4) a halogenated phenol.

U.S. Pat. No. 4,709,112 to Sato, Ikimi, Tojima and Takahashi describes a process for dimerizing lower α-olefins which uses a catalyst system formed from (1) a trialkylaluminum compound, (2) an organic salt or complex of nickel, (3) a trivalent phosphorus compound selected from specified groups, (4) a fluorinated isopropanol, and (5) a catalyst co-activator selected from specified types of halogenated compounds.

U.S. Pat. No. 4,973,788 to Lin, Nelson and Lanier describes a process for dimerizing a vinyl olefin monomer at a selectivity of at least 85 mol percent. This is accomplished by use of a catalyst which consists essentially of 0.001–0.04 mols of trialkylaluminum per mol of vinyl olefin, and conducting the reaction at a temperature in the range of about 100°–140° C. for a time sufficient to convert at least 80 mol percent of the initial vinyl olefin to a different product. The reaction rate under these conditions is quite slow, and thus a long reaction time is required. For example it is pointed out that the time required for 90 percent conversion at 120° C. with 0.043 mols of aluminum alkyl catalyst per mol of initial vinyl olefin is about 94 hours, and that with 0.017 mols of the catalyst per mol of initial vinyl olefin the time required at 120° C. is about 192 hours. It is also shown in the patent that although the reaction is faster at 172° C. compared to 120° C., the selectivity to vinylidene dimer is only 71 weight percent compared to 90 weight percent with the same catalyst concentration but at 120° C.

The vinylidene dimerization reaction with a trialkylaluminum catalyst involves the catalytic interaction (perhaps transitory coupling) between the vinyl olefin and the aluminum alkyl. As indicated in U.S. Pat. No. 4,973,788, supra, the dimerization is has been effected at temperatures of 100°–140° C. It has now been found that at these temperatures and at even higher temperatures as well, isomerization of vinyl olefin to internal olefin can occur. This competitive reaction reduces dimerization product yield, because these isomers do not further react to produce the desired vinylidene olefin product.

Isomerization of linear 1-olefins is known to occur when trace amounts of certain metals, especially nickel, react with the aluminum alkyl catalysts during olefin displacement reactions. For example, Ziegler et al., *Justus Liebigs Ann. Chem.* Volume 629 at pages 25 and 62 (1960) mentioned using phenyl acetylene to reduce isomerization in olefin displacement reactions catalyzed by nickel. To the same general effect is U.S. Pat. No. 5,124,465 to Allen, Anderson, Diefenbach, Lin, Nemec, Overstreet and Robinson. In *The Use of Aluminum Alkyls in Organic Synthesis*, Ethyl Corporation, page 53 (1977), it is stated "The isomerization of the α-olefin by the nickel catalyst can be suppressed by addition of small amounts of acetylene hydrocarbons, but by and large this modification of the displacement has not been developed to perfection."

Furthermore, ferrous metal surfaces, even if free of nickel, can cause loss of dimer selectivity in an aluminum alkyl-catalyzed vinyl olefin dimerization process.

It would be extremely desirable to be able to achieve high selectivity to vinylidene dimer without requiring use of the extremely long reaction periods deemed necessary in accordance with the process of U.S. Pat. No. 4,973,788 and without need for multicomponent catalyst systems such as described in U.S. Pat. Nos. 4,155,946 and 4,709,112. It would be particularly desirable if these objectives could be achieved while at the same time enabling the reaction to be performed with high dimer selectivity in ferrous metal-containing reaction vessels and related auxiliaries such as transfer lines and the like.

The present invention has accomplished this goal.

SUMMARY OF THE INVENTION

In accordance with this invention, it has been found that it is possible to produce vinylidene dimer with high selectivity without requiring the long reaction periods which were deemed critical in the process of U.S. Pat. No. 4,973,788 using a trialkylaluminum compound as the sole catalyst component charged to the reaction vessel. Moreover this high dimer selectivity can be achieved even though the reaction mixture is in contact with ferrous metal-containing surfaces in the reaction system. All of this can be accomplished by dimerizing vinyl olefin with at least one trialkylaluminum compound as the catalyst in a ratio in the range of 0.001 to 0.5 mol of trialkylaluminum per mol of the initial vinyl olefin at one or more temperatures in the range of about 100° to about 200° C. for a period of time sufficient to convert in the range of from 10 to about 99% by weight of the initial vinyl olefin to a different product with a vinylidene dimer selectivity of at least 80%, with the proviso that in conducting the process the liquid mixture in the reactor is maintained in direct contact with passivated ferrous metal-containing (preferably passivated steel alloy) interior reaction equipment surfaces for a substantial portion of the total period of time, e.g., at least 50% of the time (and most preferably during substantially the entire time, e.g., at least 90% of the time) that the reactor contents are at a temperature above about 50° C. In addition, the reaction mixture while hot is kept away as much as is reasonably practicable from contact with unpassivated ferrous metal-containing surfaces such as unpassivated steel reactors and related equipment. So far as is known, this invention represents the first time consideration has been focused upon the interrelationships among reaction conditions, materials of construction, and the condition of materials of construction in the conduct of an olefin dimerization process.

As noted above, it has been found that when a vinyl olefin is heated in the presence of a trialkylaluminum dimerization catalyst to a temperature at which dimerization takes place, competitive reactions can and generally do occur. For example, in addition to the desired dimer formation via the Markovnikov route, vinyl olefin can be also be dimerized to deep internal olefin dimer via the competitive anti-Markovnikov route. Also, vinyl olefin can be isomerized to internal isomer olefin via aluminum hydride route or by other known mechanisms. Moreover, it has now been found that the composition and condition of the contacted surfaces of the reactor and of reactor auxiliaries such as piping, valves, agitators, and the like contacted by the hot reaction mixture can have a profound effect upon the outcome of the dimerization reaction. In a dimerization process competitive internal olefin formation adversely affects dimer selectivity, and deep internal olefin dimer formation adversely affects final vinylidene olefin purity. However, despite the existence of such adverse competitive reactions, the practice of this invention now makes possible substantial enhancement of vinylidene dimer selectivity and suppression of isomerization to internal olefins.

Another feature of this invention is that although aluminum to hydrogen bonds serve as catalysts for isomerization of a 1-olefin to an internal olefin, and although the rate at which trialkylaluminum compounds dissociate into olefin and dialkylaluminum hydride rapidly increases with increasing temperature, the process of this invention enables the formation of vinylidene olefin products of almost as high a purity as the process of U.S. Pat. No. 4,973,788 in much shorter reaction periods.

Still another feature of the process of this invention is that it takes advantage of the exothermic nature of the olefin dimerization reaction. For example, the heat of reaction is about 20 Kcal per g mol of dimer formed. Thus by operating in the above temperature range, external energy requirements and costs are reduced, and when operating within particularly preferred temperature ranges (145° to 170° C.) such energy requirements and costs can be kept to a minimum.

There are three preferred general modes in which the process of this invention can be carried out. One such mode involves use of a single reactor commonly referred to as a "stirred pot reactor" in which the reaction is conducted with agitation on a batch basis. In another such mode the reactor comprises at least two closed vessels in which the reaction is conducted with agitation and continuous feed, the vessels being connected in series such that the feed rate to the first vessel, and the discharge rates from each vessel to the ensuing vessel, where there is an ensuing vessel, are substantially equal to each other. The third mode utilizes a single continuous elongated reactor in which the reaction is conducted with agitation on a continuous basis. When conducting the first or third of these modes it is particularly preferred to perform the reaction such that during at least 50 percent of the time that the reaction mixture is at a temperature above about 110° C.:

a) the vapor space in the reactor is in the range of 0 to 40 percent (preferably in the range of 0 to 30 percent, more preferably no more than 20 percent, and most preferably no more than 10% at most) of the total interior free space of the reactor, and b) the remainder of the free space in the reactor contains an inert atmosphere.

In the case of the second above mode of operation, the reaction is most preferably conducted such that during at least 50 percent of the time that the reaction mixture is at a temperature above about 110° C. in one or more of the vessels:

a) the total vapor space in such vessels is in accordance with the ranges given above, e.g., it is in the range of 0 to 40 percent, and most preferably it is at most no more than 10 percent, of the total interior free space of the vessels, and b) the remainder of the free space in the vessels contains an inert atmosphere.

In another preferred embodiment the process is conducted whereby the relationship among vinyl olefin conversion, reaction time and catalyst concentration is in accordance with the expression:

$$X = 1 - \exp\{-k[alR]t\}$$

where k is a rate constant which is a function of temperature, and is in terms of liters per gram mol per hour;

[alR] is the molar concentration of aluminum alkyl;

t is reaction time in hours; and

X is vinyl olefin conversion as defined by the expression:

$$1 - [Vi]/[Vi]_o$$

where

[Vi] is the vinyl olefin molar concentration at time t; and $[Vi]_o$ is the initial vinyl olefin molar concentration.

These and still other embodiments and features of this invention will become still further apparent from the ensuing description and appended claims.

FURTHER DETAILED DESCRIPTION OF THE INVENTION

The vinyl olefins used in the process can be one or more linear vinyl olefins or one or more branched chain vinyl olefins or any mixture of these. Minor amounts of internal and/or vinylidene monoolefins (e.g., up to 40 mol % of an olefin mixture) can be present in the initial vinyl olefin charged to the reactor. The amount of such internal and/or vinylidene olefins, if any, is of course excluded from consideration when calculating the mol ratios of catalyst to initial vinyl olefin used in the process. Typically the vinyl olefins used in the process will contain in the range of about 3 to about 30 or more carbon atoms per molecule. Preferably the initial vinyl olefin will contain in the range of 6 to 20, and still more preferably in the range of 8 to 16 carbon atoms per molecule. For some end use applications, it is desirable to use a substantially pure single vinyl olefin, such as 1-butene, 1-pentene, 1-hexene, 1-octene, 1-decene, or 1-tetradecene. For other end use applications mixtures of vinyl olefins are entirely suitable. In such case co-dimerization (a special case of dimerization) takes place.

Any trialkylaluminum compound can be used as the sole catalytic component charged to the dimerization reaction zone in the practice of this invention. Typically the alkyl groups will contain from 1 to 30 carbon atoms, and preferably in the range of 2 to about 18 carbon atoms each. Most preferred are trialkylaluminum compounds in which substantially all of the alkyl groups are a straight chain primary alkyl groups having in the range of from 2 to about 14 carbon atoms, such as triethylaluminum, tripropylaluminum, tributylaluminum, trihexylaluminum, trioctylaluminum, tris(decyl)aluminum, tris(tetradecyl)aluminum, and the like. Mixtures of aluminum trialkyls can be also used if desired. Changes in the composition or precise identity of the trialkylaluminum catalyst as compared to the composition and identity of the catalyst as charged to the reactor may occur as a matter of course during the conduct of the reaction, and it will be understood and appreciated that any such changes are within the scope of this invention since such changes, if they occur, are a natural consequence of the practice of the invention.

The hydride content, if any, of the aluminum trialkyl should be quite low, e.g., the aluminum trialkyl should have a maximum aluminum hydride equivalent of not more than about 0.8% In preferred embodiments the aluminum trialkyl as fed to the process is essentially hydride-free, i.e., the trialkylaluminum product contains, if any, a maximum of 0.10 wt % of aluminum hydride equivalent, and more preferably a maximum of 0.05 wt % of aluminum hydride equivalent, because the aluminum hydride bond can cause isomerization of 1-olefins to internal olefins.

It is preferred to conduct the process using in the range of about 0.001 to about 0.2 mol of trialkylaluminum per mol of the initial vinyl olefin, and even more preferably about 0.01 to about 0.05 mol of trialkylaluminum per mol of the initial vinyl olefin.

Preferably the dimerization is conducted predominately (more than half of the reaction period) at one or more temperatures in the range of about 120° to about 180° C., more preferably in the range of above 140° to about 180° C., and particularly in the range of 145° C. to 170° C. and even more preferably in the range of 160° to 170° C., in all such cases with reaction periods in the range of 1 to 24 hours sufficient to convert 10 to 99% (preferably at least 60% and most preferably at least 80%) by weight of the initial vinyl olefin to a different product. Reaction periods longer than 24 hours can be used, but are distinctly less desirable in a commercial operation. An especially preferred embodiment involves conducting the dimerization predominately at temperatures in the range of about 165°±3° C. with reaction periods in the range of about 6 to about 12 hours sufficient to convert at least 85% by weight of the initial vinyl olefin to a different product.

The reaction should be conducted in an environment that is essentially anhydrous and substantially free of oxygen and air. Aluminum trialkyls can react violently with water or compounds containing hydroxyl groups such as alcohols. Thus even a small amount of water, alcohol, or the like, in the system will inactivate some of the aluminum trialkyl. If it known that some water is present in the vinyl olefin, by use of analysis such as Karl Fischer water analysis, the amount of aluminum alkyl catalyst can be increased to compensate for the water or other active hydrogen component such as alcohol whereby the proper amount of active aluminum trialkyl catalyst remains in the system even after part of the initial aluminum alkyl has been destroyed by the water or other active hydrogen compound. Alternatively, the olefin feed can be pretreated to remove water or alcohol contamination. Likewise the process should be conducted under a dry inert atmosphere e.g., nitrogen, argon, neon, or the like, to prevent catalyst destruction.

It is desirable to have good mixing in the reactor to ensure uniform temperature. In order to avoid high reactor skin temperature, it is desirable to set the temperature of the reactor heating medium at (or close to) the desired reaction temperature. Both heat from the heating medium and heat of reaction are utilized to bring the reaction mixture from room temperature to the reaction temperature. When the reactor temperature is higher than the temperature of the heating medium, the heat transfer direction will be reversed, i.e., from reaction mixture to the heating medium. Thus, the same heating medium at almost the same temperature may be used both as the heating medium during heat up to reaction temperature, and, as the cooling medium if and when the reaction temperature is passed. Either steam or other heating media such as Dowtherm may be used.

As noted above, in conducting the process of this invention the liquid reaction mixture is maintained in direct contact with passivated ferrous metal-containing surfaces of the reaction equipment during a substantial portion of the total period of time (and most preferably substantially all of the time) during which the reaction mixture is at a temperature above about 50° C. Thus for at least 50%, preferably for at least 75%, and more preferably for at least 90% of the total time the reaction mixture is at 50° C. or higher, it is kept in contact with passivated ferrous metal-containing surfaces. In addition during such time, if any, that the hot (50° C. or more) reaction mixture is not in contact with passivated ferrous metal-containing surfaces it should be kept away from contact with unpassivated ferrous metal-containing surfaces, e.g., by using glass-lined surfaces or surfaces of mild metals such as copper. Also, the materials fed to the dimerization reaction should be kept as free as possible of certain impurities such as nickel unless an acetylenic hydrocarbon passivator is used as described hereinafter. In general, suitable passivatable ferrous metals contain at least 30%, and preferably at least 50% by weight of iron.

The ferrous metal-containing surfaces when suitably passivated can be of any composition suitable for use in the fabrication of the reactors and/or auxiliaries such as piping, agitators, condensers, and the like. Thus the ferrous metals can be of various types such as, for example, wrought iron, and various suitable types and grades of steels and stainless steel alloys, and similar materials, provided only that the ferrous metal in question can be passivated as described hereinafter. The passivation of some ferrous metals having relatively high nickel contents such as some stainless steels can be difficult, and thus such materials, even if susceptible to passivation, are nevertheless not preferred for utilization in the practice of this invention. Preferred ferrous metals are passivatable low-nickel ferrous metals. By passivatable low-nickel ferrous metals is meant that the total content of nickel, if any, in such surfaces when passivated is insufficient to decrease the selectivity of the desired vinylidene olefin product formation by more than 3% (preferably no more than 2%) as compared to the selectivity of the desired vinylidene olefin product formation in a reaction conducted with the identical materials under identical reaction conditions in a scrupulously clean glass-lined reactor of equal volume and the same internal configuration with no exposure of the reactants and reaction mixture at any stage to a nickel-containing surface or material. Generally speaking, the concentration of nickel leached into, or otherwise present in, the liquid reaction mixture as impurity sufficient to cause undesirable isomerization and loss of dimer selectivity at dimerization reaction temperatures in the range of 120° C. or above is about 2 or 3 ppm (wt) or less.

Among preferred steels are the so-called mild steels, low-alloy steels and carbon steels, as long as such steels are low-nickel ferrous metals and are susceptible to passivation as described below. Most preferably the steel has no detectable content of nickel.

Preferably, the reactors themselves are fabricated from passivatable low-nickel steels or other suitable ferrous metals, most preferably carbon steels, but interior liners made from such materials can also be used, provided that to the extent reasonably practicable, the liquid contents in the reactor do not come in contact with unpassivated ferrous metal-containing surfaces, especially unpassivated nickel-containing surfaces, when the contents are at temperatures above about 50° C. For best results the feed materials and liquid reactor contents are essentially free (i.e., to the extent reasonably practicable, they are free) of nickel impurities, and do not come in contact with any nickel-containing surface and at any time regardless of the temperature of contents. Thus, materials which are not passivatable low-nickel ferrous metals or steels, and which contain substantial amounts of nickel, such as alloys that contain more than 50% of nickel, are preferably avoided. Also, feed and transfer lines and other reactor auxiliaries that contact the feeds or reaction mixtures that are not passivatable low-nickel ferrous metals or steels should be avoided whenever possible.

In general, the steels known as mild or carbon steels are composed of iron with a carbon content of less than two percent and typically other alloying elements in the range of a few tenths of one percent. When carbon steel is alloyed singly or in combination with chromium, nickel, copper, molybdenum, phosphorus and/or vanadium in the range of a few percent or less the product is generally known as low-alloy steel.

The most preferred steels for use in the practice of this invention are the carbon steels. These materials typically have a nominal composition (essential elements per A.I.S.I.-S.A.E. 1020 as reported in *Chemical Engineers' Handbook*, 5th Edition, by P. H. Perry/C. H. Chilton, and published by McGraw Hill in 1973) of 0.45% manganese, 0.25% silicon, and 0.20% carbon, with the balance being iron. Over the years, various types of carbon steels have been developed, as for example, structural and pressure-vessel steels, and according to the foregoing handbook, there are only minor metallurgical differences between these types, the important differences being in quality or tighter specifications. Thus any carbon steel suitable for the purposes at hand constitutes a preferred material for use pursuant to this invention. For detailed specifications and chemical analyses, references should be made to the ASTM Standards published by the American Society for Testing Materials. Appropriate publications by the American Society of Mechanical Engineers, the American National Standards Institute, and the American Petroleum Institute can be also be consulted, if necessary.

In conducting the process of this invention portions of the overall reaction system or train with which the feed and/or reaction mixture comes in contact when at temperatures of 50° C. or above can be composed of suitable materials other than ferrous metals susceptible to passivation. Examples of such suitable materials include glass (e.g., glass-lining) and mild metals such as copper. However from the cost-effectiveness standpoint, plant facilities composed entirely or almost entirely of ferrous metals susceptible to passivation such as carbon steel are most preferred.

As also pointed out above, the surfaces which are contacted by the feeds and reaction mixtures are passivated. There are various ways by which surface passivation may occur or be effected. For example, reactors made with materials such as some stainless steels may become passivated after a few cycles of operation, and thereafter provide increased dimer yield. Thus such stainless steel reactors may be considered for use in the practice of this invention if the poor results achieved until such passivation occurs can be tolerated. Other more desirable procedures for effecting passivation will now be described.

Fresh (i.e., thoroughly clean) suitable ferrous metal surfaces of the reactor and auxiliaries (feed lines, valves, stirrer parts, baffles, or the like) that come in contact with the reaction feeds and mixtures, especially when at temperatures above about 50° C., can be suitably pacified by exposing such surfaces at temperatures in the range of about 25° C. to about 100° C. to contact with air or oxygen for a period sufficient to form at least a passivating molecular film of oxide on the exposed surfaces. It will be appreciated that such exposures to air are normally avoided in the case of reactors in which reactions in which aluminum alkyls are used because of the hazards involved in exposing aluminum alkyls to the atmosphere.

Another method of passivation involves exposing the ferrous metal or steel surfaces to reaction mixtures containing the aluminum alkyl catalyst, to which reaction mixtures have been added one or more acetylenic hydrocarbons at elevated temperatures. The effective passivation amounts of acetylenic hydrocarbons can be quite small, and will depend in large measure to the amount of nickel exposure and/or contamination to be encountered by the hot reaction mixture.

The one or more acetylenic hydrocarbons introduced into the reaction mixture before the aluminum alkyl-containing reaction mixture is exposed to a ferrous metal surface at a temperature above about 50° C. can be an aliphatic, cycloaliphatic, and/or aromatic hydrocarbon containing at least one acetylenic triple bond. The preferred acetylenic hydrocarbons are the alkynes, such as 1-hexyne or 2-hexyne, or a branched chain compound such as 4-methyl-1-pentyne or 5-methyl-1-hexyne, or a mixture or combination thereof. Preferred are aliphatic hydrocarbons having an acetylenic group, especially those having, immediately adjacent to a carbon atom of the acetylenic triple bond configuration, a carbon atom that is substituted by two or three hydrogen atoms. Preferably the aliphatic acetylenic hydrocarbon is a straight chain alkyne having from 4 to about 10 carbon atoms in the molecule, such as 1-butyne, 2-butyne, 1-pentyne, 2-pentyne, 1-hexyne, 2-hexyne, 3-hexyne, 1-heptyne, 2-heptyne, 3-heptyne, 1-octyne, 2-octyne, 3-octyne, 4-octyne, and the analogous nonynes and decynes, and mixtures of such alkynes having the same or different number of carbon atoms in the molecule. Most preferred are the individual hexyne isomers and mixtures of two or more of such isomers. Hexyne has been found to be highly effective when added at low dosage levels in suppressing double bond isomerization without inhibiting dimerization. Moreover, hexyne is easy to handle and dispense to the reaction mixture. In addition, its low molecular weight means that for a given weight fraction, more mols of hexyne are present in the system than with larger molecules such as phenylacetylene. Also, unlike phenylacetylene, hexyne is non-carcinogenic.

The alkyne must be used in conjunction with the trialkylaluminum compound. That is, experimental work has shown that the alkyne is incapable of complexing or otherwise passivating the nickel in the absence of the trialkylaluminum compound. The mechanism by which the alkyne effects passivation of the nickel or otherwise overcomes the devastating effect nickel can have on dimer selectivity in the process is not known.

The effective nickel-passivation amounts of the alkyne hydrocarbon can be quite small, and will depend in large measure on the amount of nickel exposure or contamination to be encountered by the hot reaction mixture. In any given situation it is desirable to perform a few pilot experiments to determine the amount of acetylenic hydrocarbon that overcomes, especially at the elevated temperatures being employed, the adverse effect of the nickel-containing surface to which the reaction mixture will be exposed and/or the amount of nickel contamination that may be present in the reaction mixture. Generally speaking, the amount used is enough to result in a dimer selectivity that is not more than 3 wt % (preferably not more than 2 wt %) less than the dimer selectivity achieved under absolutely identical conditions in a clean glass-lined reactor with the sole exception that in reaction performed in the glass-lined reactor, no acetylenic hydrocarbon is added. Most preferably the amount of alkyne used will give a dimer selectivity at least equal to, if not greater than, the dimer selectivity in the reaction performed in identical fashion (without acetylenic hydrocarbon addition) in the glass-lined reactor. Typically the amount introduced at the appropriate stage of the operation will not exceed about 5000 ppm (wt), and typically amounts in the range of up to about 2500 ppm are used. Normally, the smaller the amount sufficient to effectively inhibit double bond isomerization during dimerization, the better, as this minimizes costs and maximizes product purity. However any amount which provides the passivation under the conditions at hand without adversely affecting the dimer selectivity and vinylidene purity in any material way can be used.

The use of this passivation procedure in connection with nickel-containing steels and reaction mixtures is described in detail in commonly-owned copending application Ser. No. 08/596,812, filed Feb. 5, 1996 (contemporaneously herewith). Commonly-owned copending application Ser. No. 08/596,848, filed Feb. 5, 1996 (contemporaneously herewith) describes a dimerization process in which a combination of short reaction periods and low catalyst concentrations are used under specified temperature conditions. The entire disclosures of both of the foregoing applications are incorporated herein by reference as if fully set forth herein.

If desired, both the air or oxygen method of passivation and the acetylenic hydrocarbon method of passivation can be used when carrying out a dimerization reaction in accordance with the process of this invention.

To ensure the achievement of the full benefits of this invention, it is desirable to remove surface contamination such as previous reaction residues from the ferrous metal surfaces, as well as other portions of the reaction system that come in contact with the feeds and/or reaction mixture. Clearly, any surface residues containing significant quantities of nickel should be thoroughly removed from contaminated surfaces. Likewise metal impurities in or on surfaces that contact the reactor feed or contents such as Na, Li, etc. may also enhance isomerization of vinyl olefins and should also be removed or, preferably, totally avoided wherever possible.

It will now be readily apparent that there are a number of things that should be done in order to achieve the optimum results achievable by the practice of this invention, especially when using reaction equipment that has been used previously for conducting other kinds of chemical reactions. Such matters are considered below.

Prior to feed transfer to the dimerization reactor, the reactor should be cleaned with aqueous and/or organic solvents. The pre-reaction cleanup procedures may include some of the following steps: A) Caustic or acidic wash; B) Water wash; C) Drying (removal of water); D) Heptane (or other heavy paraffin/olefin) wash; and E) Drying (removal of heptane or other heavy paraffin/olefin.) Caustic or acidic washing may introduce trace amount of impurities either from the solution or from leaching of material from the interior reactor surfaces. Therefore it is desirable to avoid use of caustic or acidic washing of reactor surfaces. In cases where hot organic solvent wash alone is sufficient to clean up the reactor, aqueous wash is not needed. But in cases where aqueous wash is needed to accomplish the reactor cleanup, use of steam cleaning or hot water wash without use of base or acid is preferred. Caustic or acidic wash should only be used if the other alternatives are inadequate in any given situation.

If the reactor history is such that caustic or acidic wash is needed, this should be followed with fresh water washes several times until the quality of final washed water is the same as (or close to) the fresh water used. This may be accomplished by measuring pH or ionic strength (such as Ni, Na, Cl, etc.). Since trace amounts of isomerization promoters can reduce dimer yield tremendously, the purest water available at the plant site (e.g., deionized water or distilled water) is preferably used. After water wash is complete and the final wash water is discharged, the reactor should be blown to dryness with by nitrogen, as any residual water in the reactor will destroy the corresponding amount of aluminum alkyl catalyst. After aqueous wash of the reactor, organic solvent wash (heptane or others) should follow. Hot heptane wash for several hours under agitation conditions can expedite the organic wash process. After heptane wash and discharge of waste heptane, the reactor is preferably purged with nitrogen to dry the reactor. Nitrogen purge with some heat in the reactor accelerates the heptane drying process. If the passivation is to be effected by use of air (or oxygen) rather than by another method such as use of an acetylenic hydrocarbon, the cleaned reactor and associated metallic equipment with which the feeds and reaction mixtures come in contact are exposed to air for at least 0.5 hour, preferably for from 0.5 to 3 hours at a temperature of at least about 20° C., such as ambient room temperature up to about 100° C. Shorter exposure periods can be used when employing pure oxygen for surface passivation.

After all of the heptane (or other heavy paraffin/olefin) is removed and the steel surfaces passified by contact with air or oxygen (if this particular method of passivation has been selected), the dimerization reactor should be maintained with 10 psig $N_2$ at room temperature. All further processing is performed under a blanket of dry inert gas, preferably a nitrogen blanket.

Whenever possible, the feed transfer lines should be treated with the same diligence as the reactor pretreatment procedure to ensure that no contamination of feeds occurs from the transfer lines.

After the dimerization reactor and associated feed transfer lines have been cleaned up and passified by contact with air or oxygen (if this particular method of passivation has been selected for use), it is desirable to conduct a blank isomerization operation. This involves charging the reactor under a $N_2$ blanket or purge with vinyl olefin feed of the type to be used for dimerization. In the absence of trialkylaluminum catalyst, the olefin feed is then heated to 165° C. and kept at that temperature for about 12 hours. Such a blank isomerization test makes it possible to determine if there is any isomerization activity in the system in the absence of the trialkylaluminum catalyst. Pilot plant experience has indicated that there is no isomerization in the above glass-lined reactor during such a blank isomerization test even if coupons of carbon steel and/or stainless steel coupons are present in the reactor.

If heavy olefin such as tetradecene is used in the reactor pretreatment, a blank isomerization test can be also carried out with the hot heavy olefin during the reactor cleanup.

The reactor must pass a blank isomerization test before proceeding to dimerization. If it does not, the reactor can be cooked for another 24–48 hours using the same olefin to remove any residual materials which may not be completely removed during the reactor pretreatment. Then another blank isomerization test should be conducted using another fresh charge of the olefin feed. If this blank isomerization test still fails, further investigation is required to determine the cause. In this connection, failure in a blank isomerization test is deemed to be the formation in the olefin of 0.5% by weight or more of internal olefin as determined by NMR.

After achieving a satisfactory blank isomerization test, the specified amount of trialkylaluminum is charged and mixed with the vinyl olefin in the reactor containing 90 wt % of the specified total amount olefin feed to be used in the reaction. Then the remaining amount of vinyl olefin (10 wt % of specified total olefin feed) is charged to flush out any trialkylaluminum which may be trapped in the feed transfer line.

A preferred series of process steps includes: A) Batch dimerization; B) Caustic wash; C) Phase separation; and D) Distillation. These steps are briefly discussed below.

Batch dimerization is most preferably carried out at 165° C. using substantially pure linear alpha-olefin (LAO) as the vinyl olefin feed and a charge of triethylaluminum (TEA) (preferably a low hydride grade) as the catalyst. At a TEA/LAO feed molar ratio of 0.0167, reaction under these conditions typically achieves 90% LAO conversion in 12 hours reaction time. During the dimerization of an alpha-olefin (e.g., 1-octene), TEA will be converted at least in part to trialkylaluminum in which the alkyl groups correspond to the alpha-olefin (in this example, to tri-n-octyl aluminum).

In conducting the dimerization reactions of this invention it is desirable to have a low volume of vapor space to minimize isomerization in the vapor phase which in turn can reduce selectivity to dimer formation. In general the vapor space or free space in the reactor will fall in the range of 0 to 40%. Preferably, the feed charge is such that at reaction temperature, the liquid phase occupies at least 70%, more preferably over 80%, still more preferably 90% or more, and most preferably at least about 95% or more, of the internal reactor volume.

The catalyst can be, and preferably is, recovered from the reaction product and recycled to the dimerization reactor.

The following Examples illustrate the results and advantages that can be achieved by the practice of this invention as well as the importance of the operating conditions and materials used pursuant to this invention. As indicated, these Examples are intended to illustrate, and should be understood to illustrate, and not limit this invention. All reactions in these Examples reactions were conducted in a 30-gallon glass-lined Pfaudler reactor in order to clearly demonstrate the process features under evaluation. All reactions and blank runs were performed with continuous agitation under dry nitrogen atmospheres. All parts and percentages are by weight unless otherwise specified.

EXAMPLE 1

Part A. The reactor, which had been used in prior reactions, was washed with 198 pounds of heptane. The interior reactor walls were observed to have white, yellow and black deposits on them. To the reactor with such deposits in place was charged 150 pounds of 1-octene in order to conduct a blank run. The temperature of the sealed reactor was raised to and held at 165°–170° C. for a total of 69 hours. Samples of the octene were taken when the temperature reached had 165° C., and 3.5, 34, 56 and 69 hours later, and these samples as well as a sample of the 1-octene after feed to the reactor but before application of heat, were analyzed for impurities. The contents of Al, Fe and Na increased during the heating period from 0.6 to 1.8 ppm, from <0.3 to 0.44 ppm, and from 3.7 to 12.6 ppm, respectively. The analysis for nickel remained at <1 ppm throughout. No isomerization was observed.

Part B. Then, to the reactor contents was added 2.87 pounds of high purity triethylaluminum (low hydride grade with a product specification for aluminum hydride equivalent of 0.10 wt % maximum.) along with 10 pounds of 1-octene to flush the intake lines. The reaction mixture was heated and held at 165°–170° C. for 42 hours while taking samples for analysis at periodic intervals. Results of the analyses are shown in Table 1. The term "Vi Conv." represents the conversion of vinyl olefin, "Dimer Sel." means the selectivity of dimer formation, and "Vd Purity" is the purity of the vinylidene olefin formed.

TABLE 1

| Time | 8 Hrs. | 15 Hrs. | 24 Hrs. | 33 Hrs. | 42 Hrs. |
| --- | --- | --- | --- | --- | --- |
| Vi Conv. % | 73.59 | 95.06 | 97.91 | 98.14 | 99.32 |
| Dimer Sel., % | 90.98 | 89.63 | 91.76 | 88.91 | 87.85 |
| Vd Purity, % | 91.62 | 91.62 | 91.62 | 91.62 | 91.62 |

EXAMPLE 2

Part A. Another run similar to that of Example I was conducted in the same autoclave as the next consecutive run. However in this case no initial heptane wash was used. The solid residues on the interior wall surfaces contained higher amounts of Al, Fe, and Na than the residues in Example I. Ni content remained below 1 ppm, however. To the sealed reactor which had been blown dry with nitrogen and which contained a nitrogen atmosphere was charged 150 pounds of 1-octene. The sealed reactor was heated for 17 hours after reaching 165°–170° C. No reaction was observed.

Part B. To the sealed reactor contents was added 2.8 pounds of the high purity triethylaluminum, and the lines were flushed with an additional 10 pounds of 1-octene. In this case samples for analysis were taken when the reaction mixture reached 165°–170° C. (termed 0 hours), 17 hours later at which time the heating was discontinued, and at the time the reaction mixture had cooled to approximately room temperature. Table 2 gives results of these analyses.

TABLE 2

| Time | 0 Hrs. | 17 Hrs. | After Cooling |
| --- | --- | --- | --- |
| Vi Conv. % | 17.14 | 97.22 | 97.01 |
| Dimer Sel., % | 85.34 | 75.81 | 74.90 |
| Vd Purity, % | 92.53 | 92.53 | 92.52 |

EXAMPLE 3

Part A. Another run was made in the same reactor. But in this case after draining the contents, the reactor was initially blown dry with nitrogen, then the reactor interior was washed with 190 pounds of heptane. After this, the reactor interior was washed with 25% aqueous caustic solution, rinsed with water under pressure and then rinsed with acetone and dried. The reactor interior was visually clean and shiny. A coil made from clean carbon steel wire 200 feet in length which had not been exposed to air after cleaning was inserted into the reactor under nitrogen. This coil provided a surface area of approximately 8 square feet. The reactor was sealed and flushed with a nitrogen atmosphere, followed by addition of 165 pounds of a mixture of $C_{14}$ olefins containing 79.4% vinyl olefin. The contents of the sealed reactor were then heated to 165°–170° C. and held at that temperature for 16 hours. No reaction (isomerization or otherwise) was observed. Analysis of samples drawn from the reactor gave Al values of <0.5 to 1.1 ppm, Na values of <4.0 ppm, and Ni values ranging from <0.5 to <0.9 ppm.

Part B. The cooled sealed reactor was drained, recharged with 150 pounds of 1-octene while maintaining the inert nitrogen atmosphere therein. The contents were then heated to 165°–170° C. and held there for 12 hours. Analyses indicated that essentially no reaction (isomerization or otherwise) occurred.

Part C. To the contents of the cooled reactor which remained sealed was then charged 2.8 pounds of the high purity triethylaluminum as catalyst. The feed lines were flushed by addition via the feed lines of 10 pounds of 1-octene to the reactor. The sealed reactor was again heated to 165°–170° C. and held there for 12 hours after reaching 165°–170° C. Table 3 shows analytical results on samples periodically taken from the reactor.

TABLE 3

| Time | 0 Hrs. | 1 Hr. | 3 Hrs. | 6 Hrs. | 9 Hrs. |
| --- | --- | --- | --- | --- | --- |
| Vi Conv. % | 25.89 | 54.89 | 80.91 | 93.70 | 96.50 |
| Dimer Sel., % | 59.56 | 52.46 | 51.39 | 49.39 | 49.51 |
| Vd Purity, % | 93.35 | 93.35 | 93.35 | 93.35 | 93.35 |

The results of Example 3 in Table 3 show that the unpassivated carbon steel greatly reduced the selectivity to dimer formation.

EXAMPLE 4

Another run was made in the same reactor constituting, in substance, a repeat of Part C of Example 3. As before the same coil was in the reactor under the inert nitrogen atmosphere, and the charges and reaction temperatures were as in Part C of Example 3. Table 4 gives analyses of samples of the reactor contents taken periodically, including after the reaction product had been allowed to cool to room temperature ("RT").

TABLE 4

| Time | 0 Hrs. | 1 Hr. | 3 Hrs. | 6 Hrs. | 12 Hrs. | RT |
| --- | --- | --- | --- | --- | --- | --- |
| Vi Conv. % | 29.28 | 52.14 | 82.28 | 94.19 | 97.97 | 98.11 |
| Dimer Sel., % | 72.34 | 64.86 | 60.54 | 58.24 | 56.34 | 56.03 |
| Vd Purity, % | 92.97 | 92.87 | 92.87 | 92.87 | 92.87 | 92.87 |

The results of Example 4 confirm those of Example 3.

EXAMPLE 5

Part A. After completion of the run of Example 4, the reactor was drained and blown dry with nitrogen while keeping the carbon steel coil within the reactor. Then 190 pounds of heptane was used to wash the reactor interior and drained from the reactor. Next a clean stainless steel (type 316) coil with a surface area of 0.2 square foot and which had previously been exposed to air was installed into the reactor while exposing both the carbon steel coil and the stainless steel coil to air for 30 minutes at room temperature to passivate the carbon steel and ensure passivation of the stainless steel in accordance with this invention. The nominal composition of type 316 stainless steel is 18% Cr, 11% Ni, 2.5% Mo, and with a maximum of 0.10% carbon with the balance (about 46%) being Fe. Then 165 pounds of a mixture of $C_{14}$ olefins as used in Example 3, Part A, was charged into the sealed reactor and the temperature of the system was increased to 165° C. and held there for 15 hours. Essentially no reaction occurred.

Part B. The contents of the reactor from Part A were drained and replaced under a nitrogen atmosphere with 150 pounds of 1-octene. Again the temperature was raised to 165° C. and held there for 16 hours. Once again essentially no reaction occurred.

Part C. Charged to the sealed reactor contents from Part B was 2.8 pounds of the above high purity triethylaluminum and the inlet lines were flushed into the reactor with 10 pounds of additional 1-octene, whereby the ratio of aluminum to 1-octene in the reactor was 0.017 and the vapor space within the reactor was less than 5% of the total volume of the reactor. The reaction mixture was then heated to 165° C., and held at reflux temperatures of 165°–173° C. for 10 hours after reaching 165° C. (termed "0 hours"). The reaction mixture was then allowed to cool to room temperature ("RT"). Results of this operation pursuant to this invention are summarized in Table 5.

TABLE 5

| Time | 0 Hrs. | 3.5 Hrs. | 10 Hrs. | RT |
| --- | --- | --- | --- | --- |
| Vi Conv. % | 10.96 | 56.60 | 88.69 | 88.95 |
| Dimer Sel., % | 94.42 | 96.06 | 95.37 | 95.48 |
| Vd Purity, % | 93.48 | 93.48 | 93.48 | 93.48 |

The results in Table 5 demonstrate that ferrous metals or steels having as much as 11 wt % of nickel if suitably passivated can be utilized in the practice of this invention while achieving excellent dimer selectivities and vinylidene olefin purities in short reaction periods. Thus for the purposes of this invention type 316 stainless steel qualifies as a passivatable low nickel ferrous metal.

EXAMPLE 6

With the passivated carbon steel and stainless steel coils remaining within the reactor, another run pursuant to this invention was carried out. To the drained reactor were charged 150 pounds of 1-octene, 2.8 pounds of the high purity triethylaluminum, and 10 more pounds of 1-octene as the flush for the inlet lines. The aluminum to 1-octene ratio in the reactor was 0.050 and the vapor space within the reactor was less than 5% of the total internal volume of the reactor. After raising the temperature of the reaction mixture to 165° C. (termed "0 hours), the mixture was held at 165°–167° C. for 12 hours and then allowed to cool to room temperature ("RT"). Table 6 sets forth analytical results obtained in this operation.

TABLE 6

| Time | 0 Hrs. | 3 Hrs. | 7 Hrs. | 12 Hrs. | RT |
| --- | --- | --- | --- | --- | --- |
| Vi Conv. % | 12.14 | 44.28 | 73.00 | 88.57 | 89.28 |
| Dimer Sel., % | 91.18 | 94.17 | 95.28 | 94.76 | 94.89 |
| Vd Purity, % | 93.77 | 93.77 | 93.77 | 93.77 | 93.77 |

The results of Table 6 provide further confirmation of the excellent results achievable by the practice of this invention.

EXAMPLE 7

Part A. With the above passivated carbon steel and stainless steel coils remaining within the reactor, the interior of the reactor was washed by charging 190 pounds of heptane at room temperature and draining the reactor. Then 70 pounds of 1-octene was charged and the reactor temperature was raised to 165° C. and held at 165°–173° C. for 10 more hours. Essentially no reaction (isomerization or otherwise) occurred.

Part B. On completion of the test of Part A, still another run pursuant to this invention was carried out. To the reactor containing the 1-octene and the two activated coils was charged 1.4 pounds of the high purity triethylaluminum followed by a line flush with 10 pounds of 1-octene. Thus the reactor contained a total of 80 pounds of 1-octene, and the aluminum to 1-octene ratio was 0.016. The vapor space within the reactor was approximately 50% of the total internal volume of the reactor. The reaction mixture was sampled before applying heat ("BH"), and then the mixture heated to 165° C. and another sample was taken at this point ("0 hours"). Then the reaction mixture was held at 165°–167° C. for 12 hours after reaching 165° C., and was then allowed to cool to room temperature ("RT"). Analyses of the periodically taken samples are given in Table 7.

TABLE 7

| Time | BH | 0 Hrs. | 3 Hrs. | 7 Hrs. | 12 Hrs. | RT |
|---|---|---|---|---|---|---|
| Vi Conv. % | 5.13 | 11.70 | 49.27 | 76.82 | 89.37 | 88.70 |
| Dimer Sel., % | 93.54 | 93.34 | 92.01 | 92.71 | 92.36 | 91.38 |
| Vd Purity, % | 93.49 | 93.49 | 93.49 | 93.49 | 93.49 | 93.49 |

It can be seen from the results set forth in Tables 5–7 that the passivation of the steels resulted in very substantial improvements in dimer selectivity as compared to the results in Tables 3 and 4 wherein the steel was not passivated. Comparison of the results of Table 7 with those of Tables 5 and 6 shows the desirability of operating with smaller vapor spaces in the reactor as this reduces the extent to which vapor phase reactions tend to reduce dimer selectivity.

Each and every patent or other publication referred to in any portion of this specification is fully incorporated into this disclosure by reference as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

What is claimed is:

1. A process for producing vinylidene olefin using a trialkylaluminum compound as the sole catalyst component charged to the reactor, which process comprises forming and heating a mixture of vinyl olefin and at least one trialkylaluminum compound as the catalyst in a ratio in the range of 0.001 to 0.5 mol of trialkylaluminum per mol of the initial vinyl olefin at a temperature in the range of about 100° to about 200° C. for a period of time sufficient to convert in the range of about 10 to about 99% by weight of the initial vinyl olefin to a different product with vinylidene dimer selectivity of at least 80%, with the proviso that said mixture is maintained in direct contact with passivated ferrous metal interior surfaces of and/or in said reactor for a total period of at least one hour during which the reaction mixture is at a temperature above about 50° C.

2. A process of claim 1 wherein the reactor is a single reactor in which the reaction is conducted with agitation on a batch basis.

3. A process of claim 2 wherein during at least 50 percent of the time that the reaction mixture is at a temperature above about 110° C.:
   a) the vapor space in the reactor is in the range of 0 to 40 percent of the total interior free space of the reactor, and
   b) the remainder of the free space in the reactor contains an inert atmosphere.

4. A process of claim 1 wherein the reactor comprises at least two vessels in which the reaction is conducted with agitation and continuous feed, said vessels being connected in series such that the feed rate to the first vessel, and the discharge rates from each vessel to the ensuing vessel, where there is an ensuing vessel, are substantially equal to each other.

5. A process of claim 4 wherein during at least 50 percent of the time that the reaction mixture is at a temperature above about 110° C. in said vessels:
   a) the vapor space in said vessels is in the range of 0 to 40 percent of the total interior free space of the vessels, and
   b) the remainder of the free space in said vessels contains an inert atmosphere.

6. A process of claim 1 wherein the reactor is a single continuous elongated reactor in which the reaction is conducted with agitation on a continuous basis.

7. A process of claim 6 wherein during at least 50 percent of the time the reaction mixture is at a temperature above about 110° C.:
   a) the vapor space in the reactor is in the range of 0 to 40 percent of the total interior free space of the reactor, and
   b) the remainder of the free space in the reactor contains an inert atmosphere.

8. A process of claim 1 wherein the trialkylaluminum as charged to the reaction vessel is one or more trialkylaluminum compounds in which substantially all of the alkyl groups are straight chain primary alkyl groups having in the range of from 2 to about 14 carbon atoms.

9. A process of claim 1 wherein the trialkylaluminum as charged to the reaction vessel contains, if any, a maximum of 0.10 wt % of aluminum hydride equivalent.

10. A process of claim 1 wherein the trialkylaluminum as charged to the reaction vessel is triethylaluminum.

11. A process of claim 10 wherein the triethylaluminum as charged to the reaction vessel contains, if any, a maximum of 0.10 wt % of aluminum hydride equivalent.

12. A process of claim 1 wherein the vinyl olefin charged to the reactor contains in the range of 3 to 20 carbon atoms per molecule.

13. A process of claim 1 wherein said vinyl olefin is a single vinyl olefin.

14. A process of claim 13 wherein said single vinyl olefin is in admixture with up to about 40 mol percent of internal and/or vinylidene olefins.

15. A process of claim 13 wherein said single vinyl olefin is in admixture with up to about 40 mol percent of one or more paraffinic hydrocarbons.

16. A process of claim 13 wherein said single vinyl olefin is in admixture with up to about 40 mol percent of a mixture of (a) internal and/or vinylidene olefins, and (b) one or more paraffinic hydrocarbons.

17. A process of claim 1 wherein said vinyl olefin is a mixture of two or more vinyl olefins.

18. A process of claim 17 wherein said mixture of vinyl olefins is in admixture with up to about 40 mol percent of internal and/or vinylidene olefins.

19. A process of claim 17 wherein said mixture of vinyl olefins is in admixture with up to about 40 mol percent of one or more paraffinic hydrocarbons.

20. A process of claim 17 wherein said mixture of vinyl olefins is in admixture with up to about 40 mol percent of a mixture of (a) internal and/or vinylidene olefins, and (b) one or more paraffinic hydrocarbons.

21. A process of claim 1 wherein the ratio of trialkylaluminum per mol of the initial vinyl olefin is in the range of about 0.005 to about 0.05 mol of trialkylaluminum per mol of the initial vinyl olefin.

22. A process of claim 1 wherein the ratio of trialkylaluminum per mol of the initial vinyl olefin is in the range of about 0.010 to about 0.05 mol of trialkylaluminum per mol of the initial vinyl olefin.

23. A process of claim 1 wherein the dimerization is conducted predominately at temperatures in the range of about 120° to about 180° C. with reaction periods in the range of 1 to 24 hours.

24. A process of claim 1 wherein the dimerization is conducted predominately at temperatures in the range of 145° to 170° C. with reaction periods in the range of 1 to 15 hours.

25. A process of claim 1 wherein the dimerization is conducted predominately at temperatures in the range of 160° to 170° C. with reaction periods in the range of about 6 to about 12 hours.

26. A process of claim 1 wherein at least 90 percent of the interior surfaces of the reactor that are in direct contact with the reaction mixture are composed of passivated carbon-steel alloy.

27. A process of claim 1 wherein the vinyl olefin charged to the reactor contains in the range of 4 to 20 carbon atoms per molecule, wherein the trialkylaluminum as charged to the reaction vessel is one or more trialkylaluminum compounds in which substantially all of the alkyl groups are straight chain primary alkyl groups having in the range of from 2 to about 20 carbon atoms, and wherein the trialkylaluminum as charged to the reaction vessel contains, if any, a maximum of 0.10 wt % of aluminum hydride equivalent.

28. A process of claim 27 wherein said ratio is in the range of about 0.005 to about 0.05 mol of trialkylaluminum per mol of the initial vinyl olefin, and wherein the dimerization is conducted predominately at temperatures in the range of 160° to 170° C. with reaction periods in the range of 6 to 15 hours.

29. A process of claim 28 wherein the trialkylaluminum as charged to the reaction vessel is triethylaluminum.

30. A process of claim 29 wherein the triethylaluminum as charged to the reaction vessel contains, if any, a maximum of 0.10 wt % of aluminum hydride equivalent.

31. A process of claim 27 wherein the reactor is a single reactor in which the reaction is conducted with agitation on a batch basis; and wherein during at least 50 percent of the time that the reaction mixture is at a temperature above about 110° C.:
   a) the vapor space in the reactor is in the range of 0 to 40 percent of the total interior free space of the reactor, and
   b) the remainder of the free space in the reactor contains an inert atmosphere.

32. A process of claim 27 wherein the reactor comprises at least two vessels in which the reaction is conducted with agitation and continuous feed, said vessels being connected in series such that the feed rate to the first vessel, and the discharge rates from each vessel to the ensuing vessel, where there is an ensuing vessel, are substantially equal to each other; and wherein during at least 50 percent of the time that the reaction mixture is at a temperature above about 110° C. in one or more of said vessels:
   a) the vapor space in said vessels is in the range of 0 to 40 percent of the total interior free space of the vessels, and
   b) the remainder of the free space in said vessels contains an inert atmosphere.

33. A process of claim 27 wherein the reactor is a single continuous elongated reactor in which the reaction is conducted with agitation on a continuous basis; and wherein during at least 50 percent of the time the reaction mixture is at a temperature above about 110° C.:
   a) the vapor space in the reactor is in the range of 0 to 40 percent of the total interior free space of the reactor, and
   b) the remainder of the free space in the reactor contains an inert atmosphere.

34. A process of dimerizing vinyl olefin to produce vinylidene olefin which comprises:
   a) introducing into a reactor having low nickel ferrous metal alloy interior surfaces (i) vinyl olefin to be dimerized and (ii) a trialkylaluminum compound as the sole catalyst component charged to the reactor, (i) and (ii) being proportioned to result in a ratio in the range of 0.001 to 0.05 mol of trialkylaluminum per mol of the initial vinyl olefin, thereby forming a reaction mixture;
   b) maintaining the reaction mixture (i) in direct contact with passivated ferrous metal alloy interior surfaces, and substantially free of contact with metallic non-passivated nickel-containing surfaces in said reactor, for a the total period of time of at least one hour during which the reaction mixture is at a temperature above about 50° C., and (ii) under substantially anhydrous oxygen-free conditions and at one or more temperatures in the range of 100° to 200° C. for a period of time in the range of 1 to 24 hours.

35. A process of claim 34 wherein the passivated metal alloy interior surfaces of said reactor are composed of a carbon steel.

36. A process of claim 35 wherein the reaction mixture is maintained under substantially anhydrous oxygen-free conditions at one or more temperatures in the range of about 120° to about 180° C. for a period of time in the range of 1 to 24 hours.

37. A process of claim 35 wherein the vinyl olefin to be dimerized has in the range of 4 to 20 carbon atoms, wherein the trialkylaluminum compound charged to the reactor is triethylaluminum, and wherein the reaction mixture is maintained under substantially anhydrous oxygen-free conditions at one or more temperatures in the range of 145° to 170° C. for a period of time in the range of 1 to 24 hours.

38. A process of claim 35 wherein the reactor is a single reactor in which the reaction is conducted with agitation on a batch basis, wherein during at least 50 percent of the time that the reaction mixture is at a temperature above about 110° C.:
   a) the vapor space in the reactor is in the range of 0 to 10 percent of the total interior free space of the reactor, and
   b) the remainder of the free space in the reactor contains an inert atmosphere.

39. A process of claim 38 wherein the vinyl olefin to be dimerized has in the range of 3 to 20 carbon atoms, wherein the trialkylaluminum compound charged to the reactor is triethylaluminum, and wherein the reaction mixture is maintained under substantially anhydrous oxygen-free conditions at one or more temperatures in the range of about 160° to about 180° C. for a period of time in the range of 1 to 24 hours.

40. A process of claim 34 wherein the passivated metal alloy interior surfaces of said reactor are composed of a low-nickel stainless steel.

* * * * *

UNITED STATES PATENT AND TRADEMARK OFFICE
CERTIFICATE OF CORRECTION

PATENT NO. : 5,659,100
DATED : August 19, 1997
INVENTOR(S) : Kaung-Far Lin

It is certified that error appears in the above-identified patent and that said Letters Patent is hereby corrected as shown below:

| Col. | Line | |
|---|---|---|
| 12 | 47 | in "TABLE 2" in the column "After Cooling" "92.52" should read --92.53-- |
| 13 | 45 | in "TABLE 4" in the column "0 Hrs." "92.97" should read --92.87-- |

Signed and Sealed this

Twenty-third Day of December, 1997

Attest:

BRUCE LEHMAN

Attesting Officer

Commissioner of Patents and Trademarks